United States Patent
Li et al.

(10) Patent No.: US 12,254,959 B2
(45) Date of Patent: Mar. 18, 2025

(54) IDENTIFICATION, CHARACTERIZATION, AND QUANTITATION OF CRISPR-INTRODUCED DOUBLE-STRANDED DNA BREAK REPAIRS

(71) Applicant: INTEGRATED DNA TECHNOLOGIES, INC., Coralville, IA (US)

(72) Inventors: Heng Li, Wellesley, MA (US); Gavin Kurgan, Iowa City, IA (US); Matthew McNeill, Iowa City, IA (US); Yu Wang, North Grafton, MA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 448 days.

(21) Appl. No.: 16/919,577

(22) Filed: Jul. 2, 2020

(65) Prior Publication Data
US 2021/0002700 A1  Jan. 7, 2021

Related U.S. Application Data

(60) Provisional application No. 62/952,603, filed on Dec. 23, 2019, provisional application No. 62/952,598, (Continued)

(51) Int. Cl.
*G16B 20/30* (2019.01)
*G16B 20/20* (2019.01)
(Continued)

(52) U.S. Cl.
CPC .......... *G16B 20/30* (2019.02); *G16B 20/20* (2019.02); *G16B 30/10* (2019.02); *G16B 40/20* (2019.02)

(58) Field of Classification Search
None
See application file for complete search history.

(56) References Cited

U.S. PATENT DOCUMENTS

| 9,822,407 B2 | 11/2017 | Joung et al. |
| 2012/0283110 A1 | 11/2012 | Shendure et al. |

(Continued)

FOREIGN PATENT DOCUMENTS

| WO | 2014093330 A1 | 6/2014 |
| WO | 2014143228 A1 | 9/2014 |

(Continued)

OTHER PUBLICATIONS

Aleksandar Stojmirovic', E. Michael Gertz, Stephen F. Altschul and Yi-Kuo Yu. The effectiveness of position- and composition-specific gap costs for protein similarity searches. Bioinformatics vol. 24 ISMB 2008, pp. 15-23 (Year: 2008).*

(Continued)

*Primary Examiner* — Olivia M. Wise
*Assistant Examiner* — Mary C Leverett
(74) *Attorney, Agent, or Firm* — Michael Best & Friedrich LLP

(57) ABSTRACT

Described herein is a system and process for identifying and characterizing double-stranded DNA break repair sites that are based on biological information and have improved accuracy. Also described is a sequence alignment process that uses biological data to inform the alignment matrix for position specific alignment scoring, resulting in the identification of noncanonical target sites.

9 Claims, 8 Drawing Sheets

Related U.S. Application Data filed on Dec. 23, 2019, provisional application No. 62/870,426, filed on Jul. 3, 2019, provisional application No. 62/870,471, filed on Jul. 3, 2019.

(51) Int. Cl.
G16B 30/10 (2019.01)
G16B 40/20 (2019.01)

(56) References Cited

U.S. PATENT DOCUMENTS

| | | |
|---|---|---|
| 2017/0053062 A1 | 2/2017 | Cradick et al. |
| 2017/0081679 A1 | 3/2017 | Xu et al. |
| 2017/0145486 A1 | 5/2017 | Chen et al. |
| 2017/0211142 A1 | 7/2017 | Smargon et al. |
| 2017/0253925 A1 | 9/2017 | Dobosy et al. |
| 2018/0068062 A1 | 3/2018 | Zhang et al. |
| 2018/0163265 A1* | 6/2018 | Zhang ............... C12N 15/907 |
| 2019/0062736 A1 | 2/2019 | Liu et al. |
| 2019/0119701 A1 | 4/2019 | Liang et al. |
| 2021/0123035 A1 | 4/2021 | Woodley et al. |

FOREIGN PATENT DOCUMENTS

| | | |
|---|---|---|
| WO | 2015013583 A2 | 1/2015 |
| WO | 2016030899 A1 | 3/2016 |
| WO | 2016081798 A1 | 5/2016 |
| WO | 2016138500 A1 | 9/2016 |
| WO | 2016205711 A1 | 12/2016 |
| WO | 2016205940 A1 | 12/2016 |
| WO | 2017040511 A1 | 3/2017 |
| WO | 2017066175 A1 | 4/2017 |
| WO | 2017137768 A1 | 8/2017 |
| WO | 2018119060 A1 | 6/2018 |
| WO | 2018232382 A1 | 12/2018 |
| WO | 2019051237 A1 | 3/2019 |
| WO | 2019/118949 A1 | 6/2019 |
| WO | 2019110067 A1 | 6/2019 |
| WO | 2019182037 A1 | 9/2019 |
| WO | 2019/246553 A1 | 12/2019 |
| WO | 2020178772 A1 | 9/2020 |

OTHER PUBLICATIONS

Giang T. H. Vu1, Hieu X. Cao1, Friedrich Fauser, Bernd Reiss, Holger Puchta and Ingo Schubert. Endogenous sequence patterns predispose the repair modes of CRISPR/Cas9-induced DNA double-stranded breaks in *Arabidopsis thaliana*. The Plant Journal (2017) 92, 57-67 (Year: 2017).*
Eva Karina Brinkman and Bas van Steensel. Rapid Quantitative Evaluation of CRISPR Genome Editingby TIDE and TIDER (Chapter 3 of Yonglun Luo , CRISPR Gene Editing: Methods and Protocols, Methods in Molecular Biology, vol. 1961), Mar. 2019 (Year: 2019).*
Yuanming Wang et al. Systematic evaluation of CRISPR-Cas systems reveals design principles for genome editing in human cells. Genome Biology (2018) 19:62 (Year: 2018).*
Clement, Kendell, et al. "CRISPResso2 provides accurate and rapid genome editing sequence analysis." Nature biotechnology 37.3 (2019): 224-226. (Year: 2019).*
Claudel-Renard, Clotilde, et al. "Enzyme-specific profiles for genome annotation: PRIAM." Nucleic acids research 31.22 (2003): 6633-6639. (Year: 2003).*
International Searching Authority Invitation to Pay Additional Fees and Partial Search for Application No. PCT/US2021/042733 dated Nov. 3, 2021 (16 pages).
Amit et al., "CRISPECTOR provides accurate estimation of genome editing translocation and off-target activity from comparative NGS data", Nature Communications, May 2021, vol. 12, No. 1, pp. 1-16.
Lazzarotto et al., "CHANGE-seq reveals genetic and epigenetic effects on CRISPR-Cas9 genome-wide activity", Nature Biotechnology, 2020, vol. 38, No. 111, pp. 1317-1327.

Bothmer et al., "Characterization of the interplay between DNA repair and CRISPR/Cas9-induced DNA lesions at an endogenous locus," Nature Communications, Jan. 2017, 8: 13905, 12 pages.
Cameron et al., "Mapping the genomic landscape of CRISPR-Cas9 cleavage," Nat. Methods, Jun. 2017, 14(6): 600-606.
Chari et al., "Unraveling CRISPR-Cas9 genome engineering parameters via a library-on-library approach," Nat. Methods, Sep. 2015, 12(9): 823-826.
Clement et al., "Analysis and comparison of genome editing using CRISPResso2," bioRxiv, 2018, pp. 1-20.
Dai et al., "One-step generation of modular CAR-T cells with AAV-Cpf1," Nature Methods, Feb. 2019, 16(3): 247-254.
Dobosy et al., "RNase H-dependent PCR (rhPCR): Improved specificity and single nucleotide polymorphism detection using blocked cleavable primers," BMC Biotechnology, 2011, 11:80, 18 pages.
Eyquem et al., "Targeting a CAR to the TRAC locus with CRISPR/Cas9 enhances tumour rejection," Nature, Mar. 2017, 543: 113-117.
Giannoukos et al., "UDiTaS TM , a genome editing detection method for indels and genome rearrangements," BMC Genomics, 2018, 19:212, 10 pages.
Hamieh et al., "CAR T cell trogocytosis and cooperative killing regulate tumour antigen escape," Nature, Apr. 2019, 568(7750): 112-116.
Hendel et al., "Quantifying genome-editing outcomes at endogenous loci with SMRT sequencing," Cell Rep, Apr. 2014, 7(1): 293-305.
Iyer et al., "Precise therapeutic gene correction by a simple nuclease-induced double-stranded break," Nature, Apr. 2019, 568(7753): 561-565.
Labun et al., "Accurate analysis of genuine CRISPR editing events with ampliCan Kornel," bioRxiv, Sep. 2018, 15 pages.
Li, "Minimap2: Pairwise alignment for nucleotide sequences," Bioinformatics, 2018, 34: 3094-3100.
Lindsay et al., "CrispRVariants: precisely charting the mutation spectrum in genome engineering experiments," Nat. Biotechnol., 2015, 34: 701-703.
Liu et al., "CasX enzymes comprise a distinct family of RNA-guided genome editors, " Nature, Feb. 2019, 566(7743): 218-223.
Liu et al., "CRISPR-Cas9-mediated multiplex gene editing in CAR-T cells," Cell Research, Jan. 2017, 27: 154-157.
Nobles et al., "IGUIDE: An improved pipeline for analyzing CRISPR cleavage specificity," Genome Biol, Jan. 2019, 20:14, 6 pages.
Pinello et al., "Analyzing CRISPR genome-editing experiments with CRISPResso," Nat Biotech, 2016, 34: 695-697.
Rand et al., "Headloop suppression PCR and its application to selective amplification of methylated DNA sequences," Nucleic Acids Res, Aug. 2005, 33(14): e127, 11 pages.
Robinson et al., "Integrated genomics viewer," Nat. Biotechnol., Jan. 2011, 29: 24-26.
Shen et al., "Predictable and precise template-free CRISPR editing of pathogenic variants," Nature, Nov. 2018, 563(7733): 646-651.
Tsai et al., "CIRCLE-seq: a highly sensitive in vitro screen for genome-wide CRISPR-Cas9 nuclease off-targets," Nat. Methods, Jun. 2017, 14(6): 607-614.
Tsai et al., "GUIDE-seq enables genome-wide profiling of off-target cleavage by CRISPR-Cas nucleases," Nat Biotechnol, Feb. 2015, 33(2): 187-197.
Vu et al., "Endogenous sequence patterns predispose the repair modes of CRISPR/Cas9-induced DNA double-stranded breaks in *Arabidopsis thaliana*," Plant J., Oct. 2017, 92(1): 57-67.
Wienert et al., "Unbiased detection of CRISPR off-targets in vivo using DISCOVER-seq," Science, Apr. 2019, 364(6437): 286-289.
Yan et al., "BLISS is a versatile and quantitative method for genome-wide profiling of DNA double-strand breaks," Nat. Commun., May 2017, 8:15058, 9 pages.
Zetsche et al., "Cpf1 Is a Single RNA-Guide Endonuclease of a Class 2 CRISPR-Cas System," Cell, 2015, 163(3): 759-771.
International Search Report and Written Opinion for Application No. PCT/US2020/040621 dated Oct. 8, 2020 (14 pages).
Canaj et al., "Deep profiling reveals substantial heterogeneity of integration outcomes in CRISPR knock-in experiments", bioRxiv, 2019, 43 pages.

(56) References Cited

OTHER PUBLICATIONS

Chang et al., "Non-homologous DNA end joining and alternative pathways to double-strand break repair", Nature Reviews Molecular Cell Biology, vol. 18, 2017, pp. 495-506.
Ghanta et al., "5'Modifications Improve Potency and Efficacy of DNA Donors for Precision Genome Editing", bioRxiv, 2018, 31 pages.
Gutierrez-Triann et al., "Efficient single-copy HDR by 5' modified long dsDNA donors", eLife, 2018, 15 pages.
Li et al., "Design and specificity of long ssDNA donrs for CRISPR-based knock-in", bioRxiv, 2017, 24 pages.
Roth et al., "Reprogramming human T cell function and specificity with non-viral genome targeting", Nature, vol. 559, No. 7714, 2018, pp. 405-409.
International Search Report and Written Opinion for Application No. PCT/US2021/042733 dated Jan. 3, 2022 (23 pages).
International Preliminary Report on Patentability for Application No. PCT/US2020/040621 dated Dec. 28, 2021 (7 pages).
International Preliminary Report on Patentability for Application No. PCT/US2020/057105 dated May 5, 2022 (8 pages).
International Search Report and Written Opinion for Application No. PCT/US20/57105 dated Mar. 22, 2021 (14 pages).
European Patent Office Extended European Search Report for application 20835024.9, mailed on Sep. 22, 2022 (10 pages).
Deleavey, G. F., et al. "Designing chemically modified oligonucleotides for targeted gene silencing." Chemistry & biology 19.8 (2012): 937-954.
International Preliminary Report on Patentability for Application No. PCT/US2021/0472733 dated Jan. 24, 2023 (12 pages).
Østergaard, M. E., et al. "Biophysical and biological characterization of hairpin and molecular beacon RNase H active antisense oligonucleotides." ACS chemical biology 10.5 (2015): 1227-1233.
Scoles, et al. "Antisense oligonucleotides: A primer." Neurol Genet 5: e323. (2019).
Wang Z et al. Biotechnol. Nov. 17, 2011;11:109 (Year: 2011).
Faircloth BC et al. PLoS One. 2012;7(8):e42543 (Year: 2012).
NCBI BLAST Search Results report conducted Nov. 8, 2023 showing zero identity resutls (Year: 2023) (1 page).
China National Intellectual Property Administration Notification of Second Office Action for application 202080074468.9, dated Jan. 25, 2024 (15 pages with translation).
International Search Report and Written Opinion for Application No. PCT/US2023/066917 dated Aug. 10, 2023 (13 pages).
Karst, S. M., et al. "High-accuracy long-read amplicon sequences using unique molecular identifiers with Nanopore or PacBio sequencing." Nature methods 18.2 (2021): 165-169.
China National Intellectual Property Administration Notification of First Office Action for application 202080074468.9, dated Aug. 31, 2023 (19 pages with translation).

Allen, F., et al. "Predicting the mutations generated by repair of Cas9-induced double-strand breaks." Nature biotechnology 37.1 (2019): 64-72.
Bloh Jr, Kevin M.. Establishing a consensus model for the role of genomic context in CRISPR-directed gene editing. Diss. University of Delaware, 2022. (230 pages).
Bodai, Z. et al. (2022) Targeting double-strand break indel byproducts with secondary guide RNAs improves Cas9 HDR-mediated genome editing efficiencies. Nature Communications, 13(1):2351.
China National Intellectual Property Administration. Notification of the Third Office Action for Application No. 202080074468.9, dated May 29, 2024 (17 pages with translation).
International Searching Authority Invitation to Pay Additional Fees and Partial Search for Application No. PCT/US2024/020080 dated Jul. 4, 2024 (16 pages).
Japanese Patent Office. Notice of Reasons for Refusal for Application No. 2021-577412, dated May 31, 2024 (10 pages with translation).
Japanese Patent Office. Notice of Reasons for Rejection for Application No. 2022-523896, dated Jul. 2, 2024 (15 pages with translation).
Kurgan, G., et al. "CRISPAltRations: a validated cloud-based approach for interrogation of double-strand break repair mediated by CRISPR genome editing." Molecular Therapy—Methods & Clinical Development 21 (2021): 478-491.
Möller, L. et al. (2022) Recursive Editing improves homology-directed repair through retargeting of undesired outcomes. Nature Communications, 13(1):4550.
NCBI BLAST Search Result 2 (NCBI BLAST database search, performed Mar. 28, 2024 (Year: 2024) (1 page).
Needleman, S.B. et al. "A general method applicable to the search for similarities in the amino acid sequence of two proteins." Journal of molecular biology 48.3 (1970): 443-453.
Regier, J. C. et al. "Increased yield of PCR product from degenerate primers with nondegenerate, nonhomologous 5' tails." BioTechniques 38.1 (2005): 34-38.
Smith, T.F. et al. "Comparison of biosequences." Advances in applied mathematics 2.4 (1981): 482-489.
Tatiossian, K.J. et al. (2021) Rational Selection of CRISPR-Cas9 Guide RNAs for Homology-Directed Genome Editing. Molecular Therapy, 29(3):1057-1069.
European Patent Office Extended European Search Report for Application No. 20878470.2, mailed on Oct. 15, 2024 (12 pages).
European Patent Office Partial European Search Report for Application 20878470.2, dated Jul. 24, 2024 (15 pages).
Orlando, S. J., et al. "Zinc-finger nuclease-driven targeted integration into mammalian genomes using donors with limited chromosomal homology." Nucleic acids research 38.15 (2010): e152-e152.
International Search Report and Written Opinion for Application No. PCT/US2024/020080 dated Aug. 26, 2024 (18 pages).
European Patent Office. Office Action for Application No. 20835024.9, dated Oct. 30, 2024 (9 pages).

* cited by examiner

IDENTIFICATION, CHARACTERIZATION, AND QUANTITATION OF CRISPR-INTRODUCED DOUBLE-STRANDED DNA BREAK REPAIRS

CROSS-REFERENCE TO RELATED APPLICATIONS

This application claims priority to U.S. Provisional Patent Application Nos. 62/870,426 and 62/870,471, both filed on Jul. 3, 2019 and 62/952,603 and 62/952,598, both filed on Dec. 23, 2019, the contents of which are incorporated by reference herein in their entirety.

TECHNICAL FIELD

Described herein is a system and process for identifying and characterizing double-stranded DNA break repair sites that are based on biological information and have improved accuracy. Also described is a sequence alignment process that uses biological data to inform the alignment matrix for position specific alignment scoring, resulting in the accurate identification of noncanonical target sites.

BACKGROUND

The use of targeted nucleases, such as CRISPR proteins, has transformed genome editing. CRISPR enzymes form ribonucleoproteins (RNPs) when hybridized with either 2-part crRNA and tracrRNA or single guide RNAs (sgRNAs). With either approach, a short protospacer sequence (a guide RNA or "gRNA") targets a specific sequence in a complementary molecule. Upon finding a match, these enzymes introduce a break in one or both DNA (or RNA) strands. CRISPR enzymes targeting DNA (e.g., Cas9, Cas12a/Cpf1) introduce double stranded breaks (DSBs) at predictable genomic positions relative to the gRNA's hybridization target. DNA DSBs are repaired by intracellular machinery, but the repair process often results in insertions and deletions (indels), substitutions, and other suboptimal allelic variants.

Because each cell in an affected population must repair itself independent of adjacent cells, and the specific outcome can contain different resulting alleles, the population of cells is likely to contain a plurality of alleles at the targeted location. Additionally, the targeting capability of these nucleases is often somewhat non-specific, which results in undesired mutations at other, off-target, genomic locations.

It is highly desirable to characterize and quantify the plurality of alleles at both on-target and off-target locations. Researchers often use DNA sequencing (such as Illumina next generation sequencing; NGS) to observe the resulting allelic diversity. Multiplexed polymerase chain reaction (PCR) can be performed to amplify and enrich all targeted locations. The resulting amplicons can be sequenced. The plurality of alleles can be characterized and counted using specialized software.

Many specialized software tools have been developed to characterize the allelic variants resulting from DSBs. Prior tools include CRISPResso [1], crispRvariants [2], and Amplican [3]. These tools generally work by aligning each sequence read against expected amplicon targets using the Needleman-Wunsch, bwa, or custom alignment algorithms. The algorithm generates a list of possible read: target alignments. Each alignment is scored based on the number of matching, mismatching, and missing nucleotides (gaps). The best scoring alignment is used for downstream data processing.

Alignment algorithms sometimes generate equally valued query: target alignments, which are most likely to occur when the query contains an insertion or deletion. From the equally valued options, alignment methods will return all or select one option. When selecting, some methods make the selection at random. Without a good predictive model or set of heuristic rules to make the selection, the alignment choice is variable, which can lead to incorrect indel annotations and lower accuracy results.

What is needed is an algorithm and process for identifying and characterizing double-stranded DNA break repair sites that are based on biological information and have improved accuracy.

SUMMARY

One embodiment described herein is a computer implemented process for identifying and characterizing double-stranded DNA break repair sites with improved accuracy, the process comprising executing on a processor the steps of: receiving sample sequence data comprising a plurality of sequences; analyzing and merging of the sample sequence data and outputting merged sequences; developing target-site sequences containing predicted outcomes of repair events when a single-stranded or a double-stranded DNA oligonucleotide donor is provided and outputting the target predicted outcomes; binning the merged sequences with the target-site sequences or the optional target predicted outcomes using a mapper and outputting target-read alignments; re-aligning the binned target-read alignments to the target-site using an enzyme specific position-specific scoring matrix derived from biological data that is applied based on the position of a guide sequence and a canonical enzyme-specific cut site and producing a final alignment; analyzing the final alignment and identifying and quantifying mutations within a pre-defined sequence distance window from the canonical enzyme-specific cut sites; outputting the final alignment, analysis, and quantification results data as tables or graphics. In one aspect, the sequence data comprises sequences from a population of cells or subjects. In another aspect, the enzyme-specific cut site comprises one or more of Cas9, Cas12a, or other Cas enzymes. In another aspect, the pre-defined sequence distance window is enzyme specific and comprises between 1 nt to about 15 nt. In another aspect, the results show the percent editing, percent insertion, percent deletion, or a combination thereof. In another aspect, the accuracy of identifying variant target sites is improved by about 15 to about 20% as compared to comparable processes.

Another embodiment described herein is a computer implemented process for aligning biological sequences, the process comprising executing on a processor the steps of: receiving sample sequence data comprising a plurality of sequences; aligning the sequence data to a predicted target sequence using a matrix based on an enzyme specific position-specific scoring of a specific nuclease target site; outputting the alignment results as tables or graphics. In one aspect, the sequence data comprises sequences from a population of cells or subjects. In another aspect, the specific nuclease target sequence comprises a target site for one or more of Cas9, Cas12a, or other Cas enzymes. In another aspect, the matrix uses position-specific gap open and extension penalties.

Another embodiment described herein is a method for identifying and characterizing double-stranded DNA break repair sites with improved accuracy, the process comprising: extracting genomic DNA from a population of cells or tissue from a subject; amplifying the genomic DNA using multiplex PCR to produce amplicons enriched for target-site sequences; sequencing the amplicons and obtaining sample sequence data; subsequently executing on a processor, the steps of: receiving sample sequence data comprising a plurality of sequences; analyzing and merging of the sample sequence data and outputting merged sequences; developing target-site sequences containing predicted outcomes of repair events when a single-stranded or a double-stranded DNA oligonucleotide donor is provided and outputting the target predicted outcomes; binning the merged sequences with the target-site sequences or the optional target predicted outcomes using a mapper and outputting target-read alignments; re-aligning the binned target-read alignments to the target-site using an enzyme specific position-specific scoring matrix derived from biological data that is applied based on the position of a guide sequence and a canonical enzyme-specific cut site and producing a final alignment; analyzing the final alignment and identifying and quantifying mutations within a pre-defined sequence distance window from the canonical enzyme-specific cut sites; outputting the final alignment, analysis, and quantification results data as tables or graphics. In one aspect, the enzyme-specific cut site comprises one or more of Cas9, Cas12a, or other Cas enzymes. In another aspect, the pre-defined sequence distance window is enzyme specific and comprises between 1 nt to about 15 nt. In another aspect, the results show the percent editing, percent insertion, percent deletion, or a combination thereof. In another aspect, the accuracy of identifying variant target sites is improved by about 15 to about 20% as compared to comparable processes.

DETAILED DESCRIPTION

Figure 1:
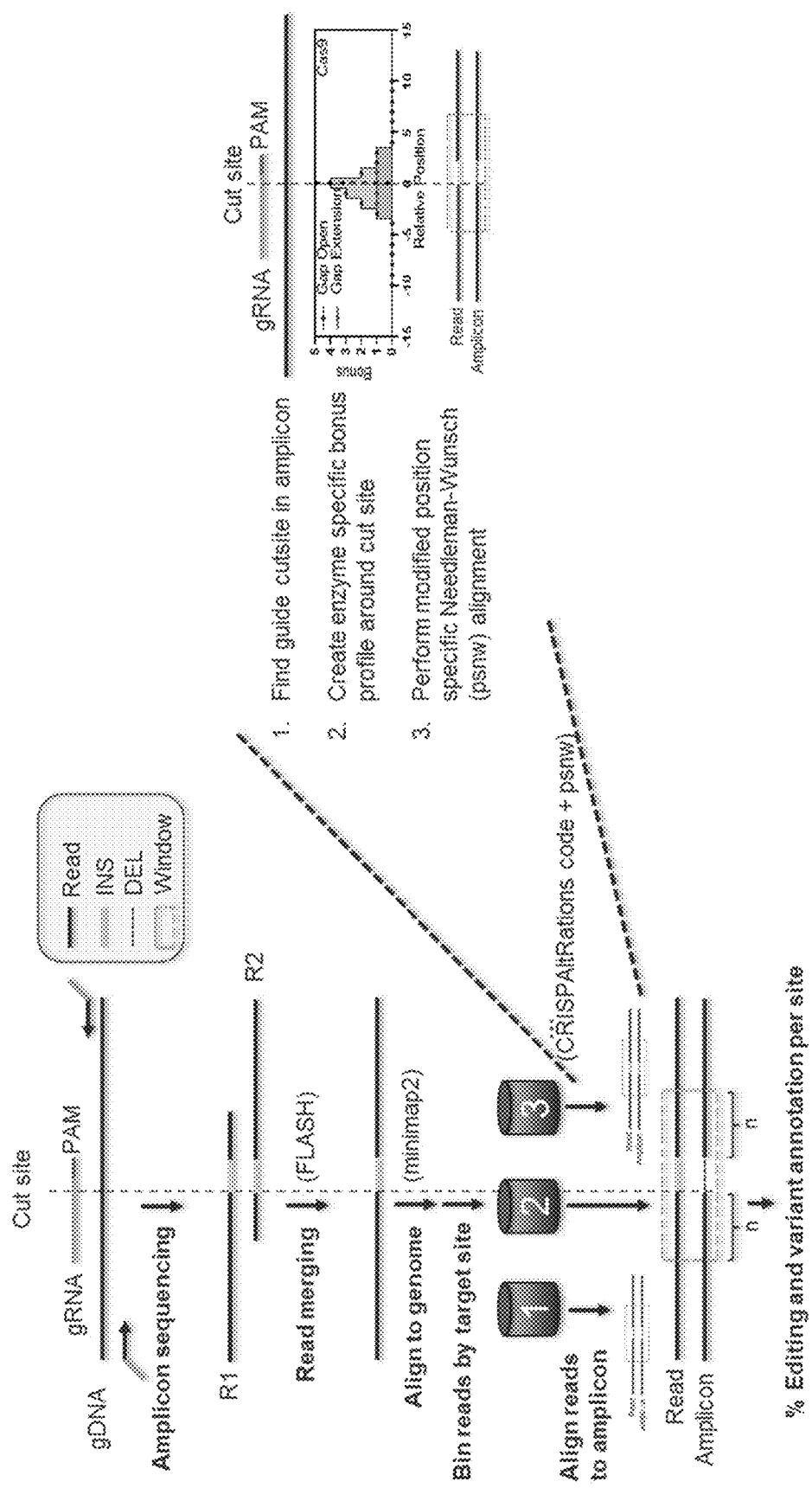
FIG. 1. General workflow for CRISPAltRations. Edited genomic DNA is extracted and amplified using targeted multiplex PCR to enrich for the on- and predicted off-target loci. Amplicons are sequenced on an Illumina MiSeq. Read pairs are merged into a single fragment (FLASH), mapped to the genome (minimap2) and binned by their alignment to expected amplicon positions. Reads in each bin are re-aligned to the expected amplicon sequence after finding the cut site and creating a position specific gap open/extension bonus matrix to preferentially align indels closer to the cut site/expected indel profiles for each enzyme (CRISPAltRations code+psnw). Indels that intersected with a window upstream or downstream of the cut site were annotated. Percent editing is the sum of reads containing indels/total observed.
Figure 2:
FIG. 2. Directed acyclic graphic of the CRISPRAltRations pipeline. Dashed boxes represent steps within the pipeline, and each step may contain one or more software tools. Lines and arrows show the flow of information through the pipeline. Two important steps are minimap2_orig_reads (orange) uses minimap2 [4] to align sequence reads against a reference genome, which is an optional step. Later, the minimap2 is used to align sequence reads against their expected target regions. The CRISPy Python tool (developed internally), re-aligns sequence reads against their target regions by calling a custom-modified version of psnw, which performs a cut-site re-alignment against the target region. CRISPy is also responsible for characterizing the detected indels in aligned reads.

One embodiment described herein is an analytical pipeline called CRISPAltRations. See FIGS. 1-2. Briefly, this pipeline takes in FASTQ files, and builds a merged R1/R2 consensus using FLASH. Simultaneously, a target site reference is built, which describes the sequences for all expected on-target locations. Optionally, a target is built that contains an expected outcome of a homology directed repair (HDR) event. Next, the merged sequence reads are aligned to the target reference sequences using minimap2, (which was originally developed for rapid alignment of long reads (e.g., those generated by the Oxford Nanopore Technologies MinION). Reads aligning to each target are then re-aligned using a modified form of the Smith-Waterman aligner. The modified aligner allows us to improve detection of insertions and deletions resulting from DSB repair. All observed variants within a pre-defined distance of the DSB location are characterized and quantified. Finally, the results are summarized in tables and graphs. The various described programs, tools, and file types (as well as those mentioned below) are familiar to and readily accessible to those having ordinary skill in the art. It should be understood that these programs, tools, and file types are exemplary and are not intended to be limiting. Other tools and file types could be used to practice the described processing and analysis.

In this analytical pipeline, the following improvements over prior methods are described. First, the use of minimap2 [4] enables alignment of reads generated from both short and long read sequencers. Second, by constructing the expected outcome of the homology directed repair event, the ability to characterize perfect (i.e., correctly occurring) HDR events is improved. Third, use of the modified Needleman-Wunsch aligner that can accept a Cas-specific bonus matrix enables significantly improved indel characterization and percent (%) editing quantification over prior methods. Fourth, graphical visualization of the introduced allelic variants is improved. Fifth, a predicted repair event, as described in a prior tool [5], is compared against the observed repair, and the molecular pathways involved in the repair can be described.

In one embodiment, the processes described herein have the following advantageous uses:

Accurate characterization of indel profiles resulting from DSBs.

The fraction of reads containing an indel after a DSB is repaired is used to calculate the percentage of editing. This metric (% editing) is used to determine the effectiveness of a gRNA for use in CRISPR-Cas gene editing.

Accurate characterization of the resulting indel similarly improves the ability to identify the percentage of cellular chromosomes in a population of cells containing a frame-shifting mutation. Frame-shifting mutations modify proteins encoded by affected genes.

Accurate characterization of inserted sequences.

Accurate characterization of multiple mutations resulting from multiple gRNA/Cas9 (i.e., ribonucleoprotein complex) deliveries or dual-guide region modifications.

Analysis of indels sequenced on a long-read platform, such as MinION. Additionally, it allows phased characterization of both ends of large (>400 nt) insertion of deletion events, which occur after DSB repair.

Improved result visualization.

One embodiment described herein is a computer implemented process for identifying and characterizing double-stranded DNA break repair sites with improved accuracy, the process comprising executing on a processor the steps of: receiving sample sequence data comprising a plurality of sequences; analyzing and merging of the sample sequence data and outputting merged sequences; developing target-site sequences containing predicted outcomes of repair events when a single-stranded or a double-stranded DNA oligonucleotide donor is provided and outputting the target predicted outcomes; binning the merged sequences with the target-site sequences or the optional target predicted outcomes using a mapper and outputting target-read alignments; re-aligning the binned target-read alignments to the target-site using an enzyme specific position-specific scoring matrix derived from biological data that is applied based on the position of a guide sequence and a canonical enzyme-specific cut site and producing a final alignment; analyzing the final alignment and identifying and quantifying mutations within a pre-defined sequence distance window from the canonical enzyme-specific cut sites; outputting the final alignment, analysis, and quantification results data as tables or graphics.

In one embodiment, edited genomic DNA is extracted and amplified using targeted multiplex PCR to enrich for the on- and predicted off-target loci. Amplicons are sequenced on an Illumina MiSeq. Read pairs are merged into a single fragment (FLASH), mapped to the genome (minimap2) and binned by their alignment to expected amplicon positions. Reads in each bin are re-aligned to the expected amplicon sequence after finding the cut site and creating a position specific gap open/extension bonus matrix to preferentially align indels closer to the cut site/expected indel profiles for each enzyme (CRISPAltRations code+psnw). Indels that intersected with a window upstream or downstream of the cut site were annotated. Percent editing is the sum of reads containing indels/total observed.

Figure 3:
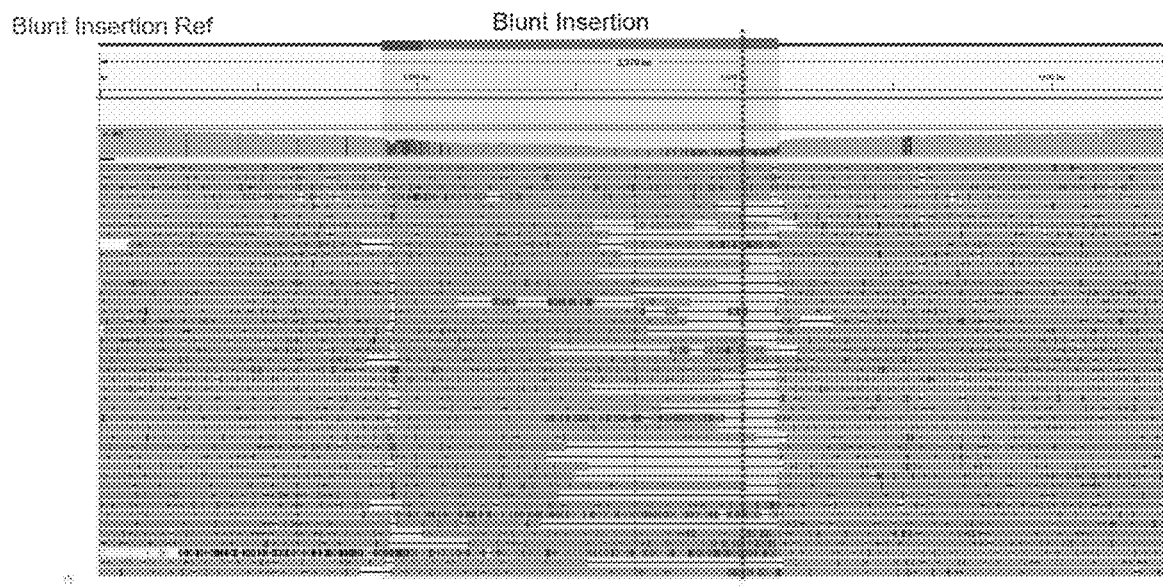
FIG. 3. MinION sequencing read data aligned to a reference target demonstrates a blunt insertion. The drop in expected coverage (grey highlight) indicates a large insertion. The mismatches on the internal edges of the grey highlight indicate mismatches between the observed read data and the expected reference.

In some embodiments, the process described herein uses minimap2 [4], which enables alignment of reads generated from both short and long read sequencers. Prior tools typically only accept short read sequencing data, such as those that are generated by Illumina sequencers. Others have used long read sequencing data to examine large insertions or deletions [6-8], but no stand-alone publicly available tools are believed to exist. Long read data handling is partially enabled by use of the minimap2 aligner. For example, the alignment results can be visualized, which shows identification of a blunt molecular insertion in DNA after a DSB repair (FIG. 3). Another embodiment sorts between real and noise-derived indels using a method similar to a previously published tool [7] in which small indels are ignored.

Figure 4:
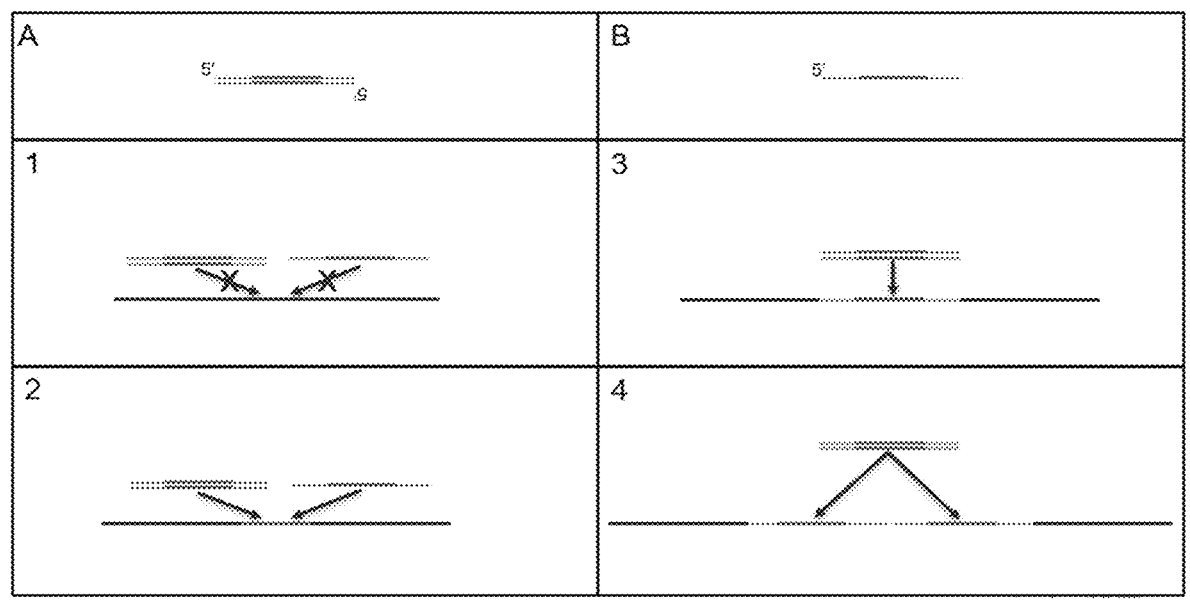
FIG. 4. Cartoon examples representing the kinds of structural variants that could occur when using a DNA oligo as a template for homology directed repair (HDR). These examples are not comprehensive. In the cartoon, blue represents the reference sequence, green represents the homology arms, and orange represents the desired inserted sequence. (A) and (B) Example double stranded and single stranded template oligos, respectively. (1) [Prefect repair] The region containing the DSB is repaired without any structural variants being introduced even when single or double stranded template oligos are present. (2) [HDR-mediated repair] The template oligo directs HDR, resulting in the desired insertion. Only the desired inserted sequence is observed in the repaired DNA. (3) [Non-homologous end joining (NHEJ) repair] the template oligo is inserted bluntly after the DSB. (4) [NHEJ repair with duplicate insertion] the template oligo is inserted bluntly multiple times after the DSB. Examples 3 and 4 are most likely to occur with a double stranded oligo used as a repair template; the homology arms present in the donor sequence are also inserted into genome.

In another embodiment, by constructing the expected outcome of the HDR event, the ability to characterize perfect HDR events is improved. A reference file, in FASTA format, contains each expected sequence target and modified sequence targets as well. The first step toward constructing this file involves creating a reference sequence index that enables reads to be aligned to each expected structural variant. For example, if one interrogates a region targeted for a DSB and double stranded DNA donor oligo to enable HDR, there are multiple different likely biological repair outcomes: perfect repair (FIG. 4-1), HDR-mediated repair (FIG. 4-2), NHEJ repair (FIG. 4-3), and NHEJ repair with duplicate insertion (FIG. 4-4). Other outcomes, such as template fragment or triple template insertions, are also possible (not shown). A similar reference file construction approach has been used by other tools, such as UDiTaS™ [9].

Figure 5:
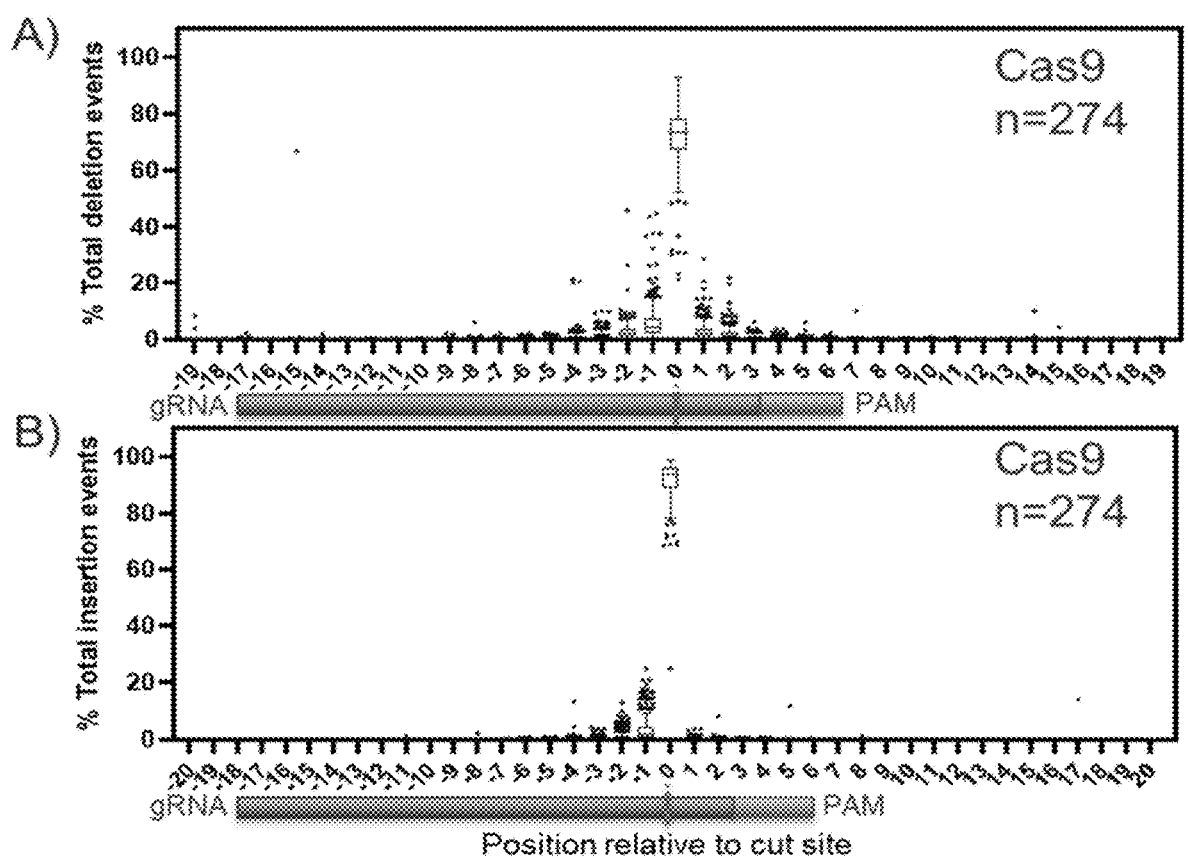
FIG. 5. Position of occurrence of editing events in Cas9 data. Position of indel occurrence from the nuclease cut site using a set of 274 Cas9 guides editing unique genomic targets in a Jurkat cell line. Both (A) deletion and (B) insertion position events were normalized by quantifying them as % total of the respective indel event within the sample. Only sites with >50 reads and >5% indels were used for analysis to limit low-confidence signal and remove noise. Indels were quantified within a 20 bp window from the cut site. Outliers were largely found to be sites that had a non-reference indel present in the Jurkat cell line that did not appear to be caused by DSB activity.
Figure 6:
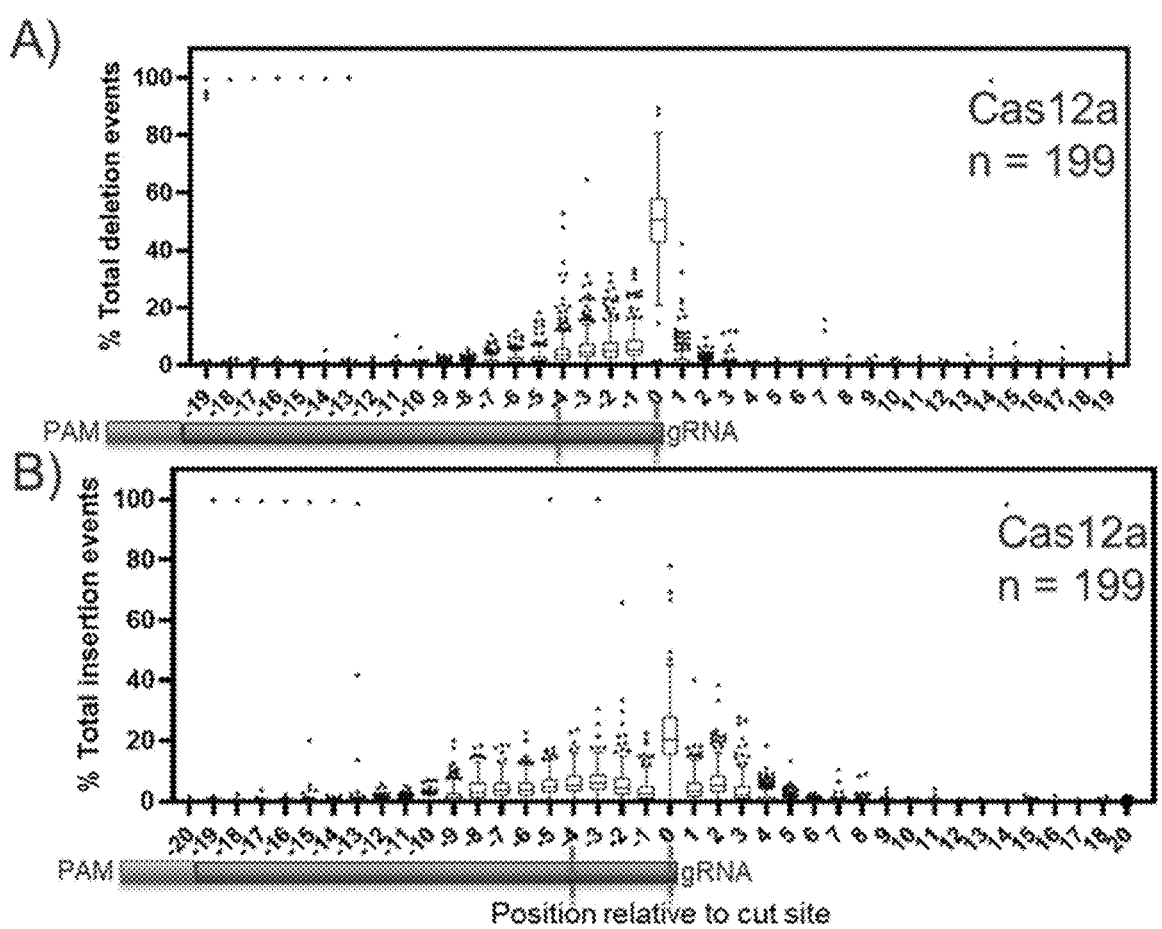
FIG. 6. Position of occurrence of editing events in Cas12a data. Position of indel occurrence from the nuclease cut site using a set of 199 Cas12a guides editing unique genomic targets in a Jurkat cell line. Both (A) deletion and (B) insertion position events were normalized by quantifying them as % total of the respective indel event within the sample. Only sites with >50 reads and >5% indels were used for analysis to limit low-confidence signal noise. Indels were quantified within a 20-bp window from the cut site. Outliers were largely found to be sites that had a non-reference indel present in the Jurkat cell line that did not appear to be caused by DSB activity.
Figure 7:
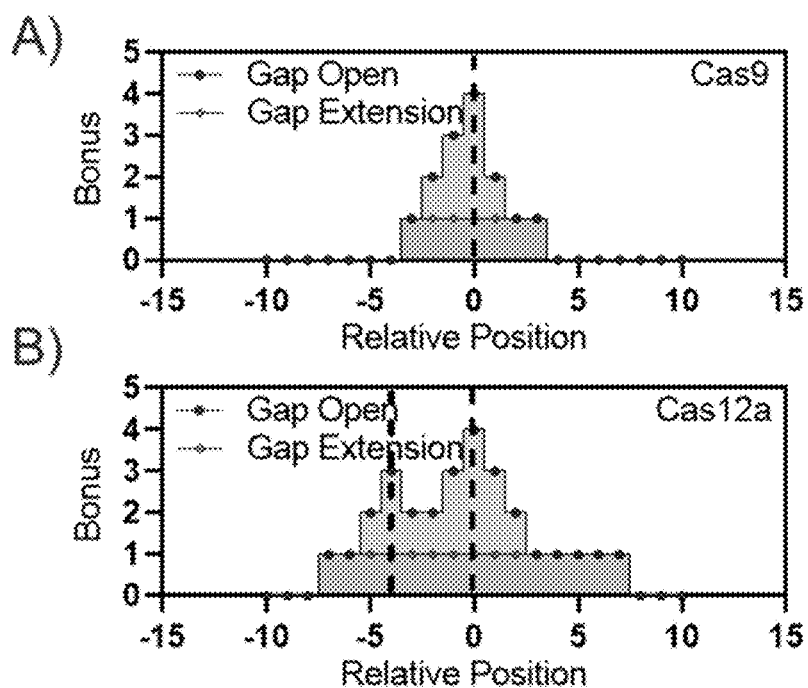
FIG. 7. Gap open/extension penalty vectors near the nuclease introduced DSB. To positively weight indels near the cut site in sequence alignments, we use a position specific matrix of values representing variable gap open or extension penalties are used, where the length of the array is equal to the integer positions of each nucleic acid in the target (thick blue lines). The vector values (red circles and blue diamonds) are varied based on the proximity to the nuclease cut site (vertical black dashed line). Thus, indels that are closest to the cut site have the least gap open or extension penalty.
Figure 8:
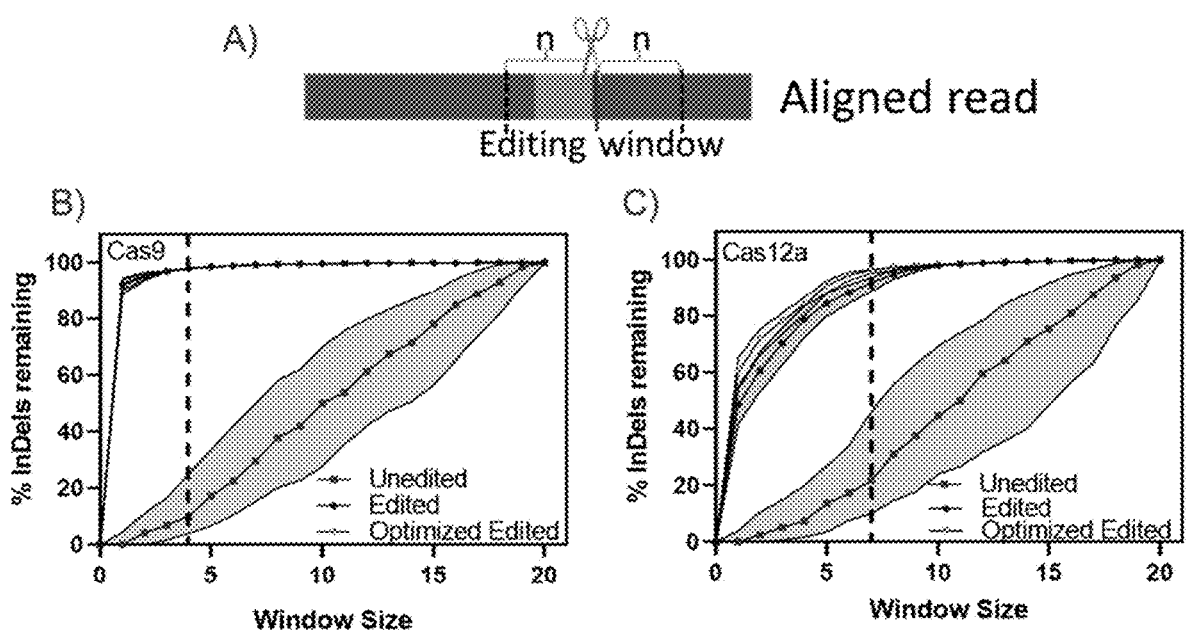
FIG. 8. Choosing an optimal window to observe true CRISPR-Cas9 editing events. (A) The editing window is a nucleotide distance around the CRISPR cut site used to identify indels. True and false editing events were calculated as % indels from targeted sequencing of cells treated or untreated for (B) Cas9 (n=263 pairs of treatment vs. control) or (C) Cas12a (n=384 pairs of treatment vs. control), respectively. Most true editing events are collected with a 4 nt window for Cas9 or 7 nt for Cas12a; while expanding the window only further collects additional false editing.

In another embodiment, a modified version of the Needleman-Wunsch algorithm is used to re-align reads against their expected target. The method described herein increases accuracy of alignments containing an indel (as annotated in alignment's CIGAR string). It significantly improves indel characterization and % editing quantification over prior methods. DNA sequence aligners such as minimap2 and Needleman-Wunsch approaches weigh indel alignments using fixed penalties for opening and extending gaps. This method is improved upon by re-aligning reads to their targets using position-specific gap open and extension penalties (enabled in a tool called "psnw") such that alignments with indels favor positioning them overlapping or near the predicted DSB. This position specific matrix is set to reflect the actual characterized indel profile of the specific Cas enzyme being used for editing (FIGS. 5-6). Thus, indel base alignments are most highly favored at or near the predicted target cut site (variable scoring strategy; FIG. 7). This method enables accurate realignment of indels, particularly those that occur in repetitive regions in the reference sequence. This approach improves the ability to identify the most biologically likely result.

A recently developed tool (CRISPResso2 [11]), uses a cut-site aware alignment strategy. However, the processes described herein implements the cut-site aware alignment method using a full gap open/extension matrix during alignment that is tuned by actual editing data at Cas9/Cas12a sites and implemented in C++. In contrast, CRISPResso2 uses a method that only enables a single bonus at the cut site and is implemented in Python.

In another embodiment, the processes described herein collect indels nearby the nuclease cut site and tag indels that intersect the cut site, or within a fixed distance. Some published accounts suggest a 1-2 nt fixed distance, but the data supporting those choices has been limited. In developing the embodiments described herein, the optimal distance (i.e., window size) around the cut site was studied using a set of Cas9-RNP treated and paired untreated control samples.

It was observed that a 4-nt window for Cas9 or a 7-nt window for Cas12a provided the greatest sensitivity and provided an acceptable specificity (FIG. 4). The larger window requirement for Cas12a is likely due to the mechanism of action; Cas12a implements a double strand break by producing two single strand breaks 5-bp away (leaving "sticky" ends) [12]. Thus, the process described herein can be expanded to other nucleases (e.g., CasX) [13] having biological data to inform the target window size and enzymatic mechanism of action.

Figure 9:
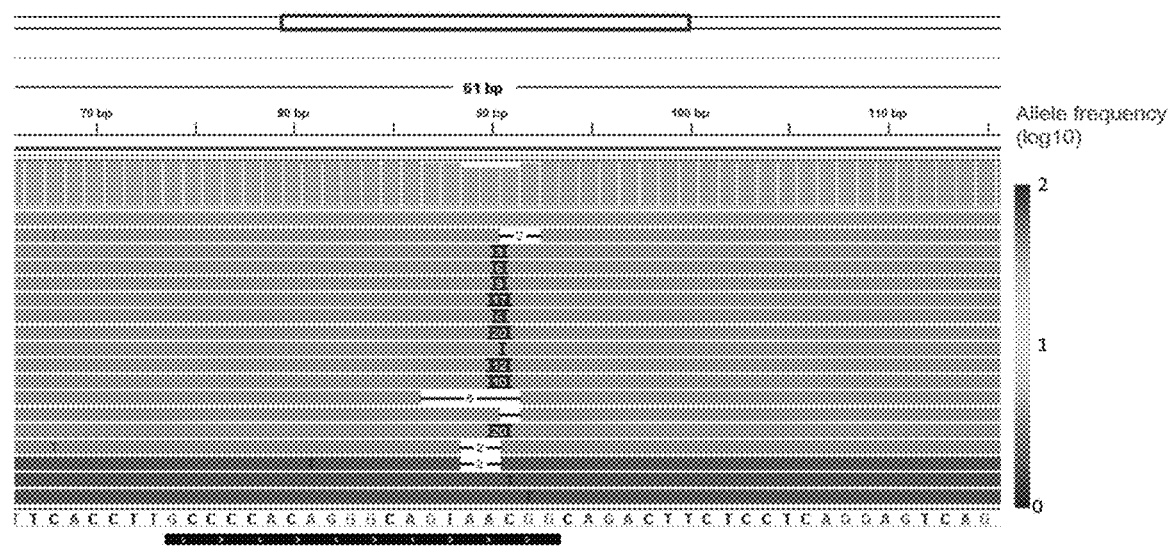
FIG. 9. Screen shot of deduplicated read alignments by observed frequency. Total region coverage is indicated by the height of the vertical gray bars (top), and reads are horizontal colored bars. Brighter colored reads indicate more frequently observed indels. Horizontal thin lines indicate deletions; vertical purple "I" symbols show insertions, and colored bars within reads indicate mismatched bases.

In another embodiment, graphical visualization of the allelic variation is improved. Downstream of the alignment step, several other analyses are performed that are unique to the described method. To generate an improved visualization, reads are deduplicated based on the identity of identified indel sequences within the CRISPR editing window post-alignment. Deduplicated reads are written back to a BAM file, and the frequency of each deduplicated read within the original population of reads is written to an associated BAM tag. After the file is indexed, indels in deduplicated reads and their associated frequencies can be visualized using the commonly available IGV tool [10] (FIG. 9).

In another embodiment, a predicted repair event is compared, as described in a prior tool [5], against the observed repair, and can be used to determine the molecular pathways involved in the repair. The system described herein also adds the ability to compare the observed indel profile against expected indel profiles, which enables rapid discernment about whether an experimental treatment modified the intracellular mechanisms of DNA repair.

Figure 10:
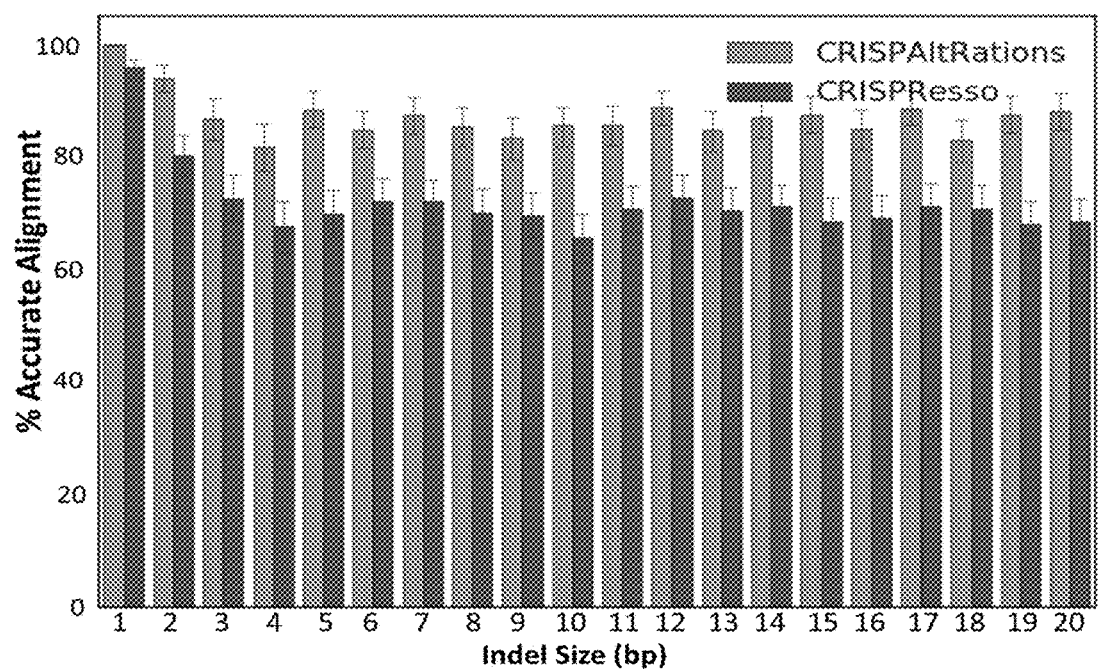
FIG. 10. CRISPAltRations reliably finds the correct indel. Each bar reports the percentage of correctly returned indels. Using synthetically generated data representing 12,060 unique indel events, evenly distributed between each size bin (x-axis) and 603 unique amplicons. Error bars represent the 95% confidence interval across targets.
Figure 11:
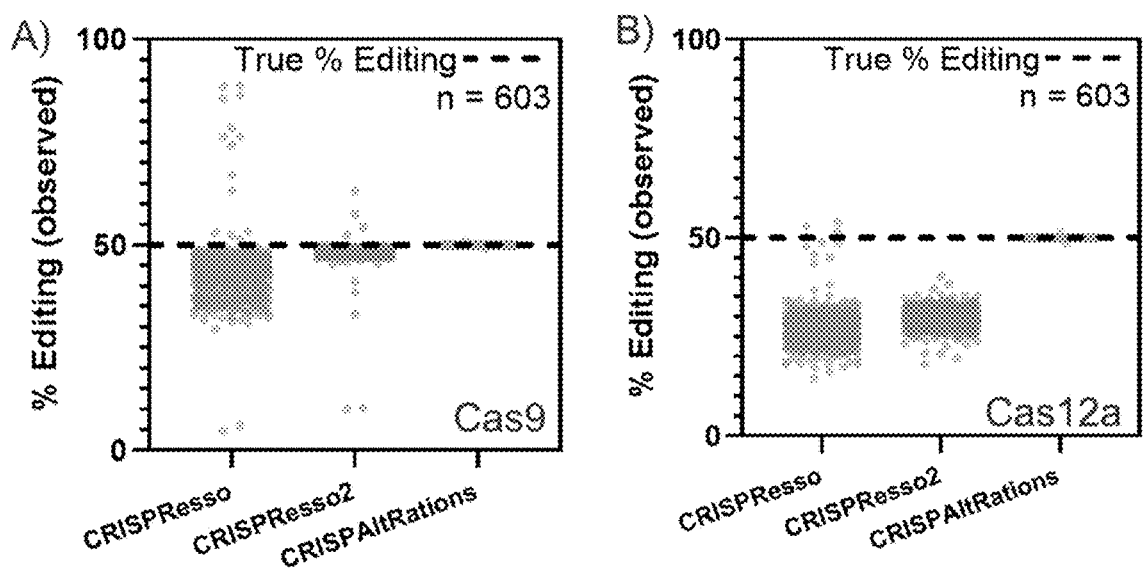
FIG. 11. CRISPRAltRations more accurately reports the total % editing at the 603 synthetic targets with simulated (A) Cas9 or (B) Cas12a editing. Dots represent the percent editing observed at each target site, and the horizontal line represents the percent indels introduced at each target in the generated synthetic data. CRISPResso2Pooled and CRISPResso1Pooled were run using default pipeline parameters for each panel with the required minimal read depth for quantification removed (to prevent incorrect drop-out of amplicons).

The utility of the system and methods described herein is demonstrated by generating a synthetic set of 603 gRNA: amplicon pairs. At each target, 4000 read pairs (2×150 bp) are synthetically generated with a simulated Illumina MiSeq v3 platform error profile. In half of the reads, random indels are introduced based on a model generated off the observed editing profile for Cas9 and Cas12a (FIGS. 4-5). The synthetic data is analyzed using the CRISPRAltRations system described herein and the previously published CRISPResso1 and CRISPResso2 tools [11]. By implementing the method described herein, the ability to correctly characterize indels is improved by ~15-20% (FIG. 10). The algorithm described herein has increased accuracy because it produces a biologically informed selection of the best alignment in targets where multiple equally scored alignments are possible. Additionally, the method described herein more accurately calculates the percentage of modified DNA molecules (FIG. 11). The process and strategy described herein is an important enhancement toward characterizing and quantifying indels introduced after DSB repair.

Another embodiment described herein is a computer implemented process for aligning biological sequences, the process comprising executing on a processor the steps of: receiving sample sequence data comprising a plurality of sequences; aligning the sequence data to a predicted target sequence using a matrix based on an enzyme specific position-specific scoring of a specific nuclease target site; outputting the alignment results as tables or graphics. In one aspect, the sequence data comprises sequences from a population of cells or subjects. In another aspect, the specific nuclease target sequence comprises a target site for one or more of Cas9, Cas12a, or other Cas enzymes. In another aspect, the matrix uses position-specific gap open and extension penalties.

Another embodiment described herein is a method for identifying and characterizing double-stranded DNA break repair sites with improved accuracy, the process comprising: extracting genomic DNA from a population of cells or tissue from a subject; amplifying the genomic DNA using multiplex PCR to produce amplicons enriched for target-site sequences; sequencing the amplicons and obtaining sample sequence data; subsequently executing on a processor, the steps of: receiving sample sequence data comprising a plurality of sequences; analyzing and merging of the sample sequence data and outputting merged sequences; developing target-site sequences containing predicted outcomes of repair events when a single-stranded or a double-stranded DNA oligonucleotide donor is provided and outputting the target predicted outcomes; binning the merged sequences with the target-site sequences or the optional target predicted outcomes using a mapper and outputting target-read alignments; re-aligning the binned target-read alignments to the target-site using an enzyme specific position-specific scoring matrix derived from biological data that is applied based on the position of a guide sequence and a canonical enzyme-specific cut site and producing a final alignment; analyzing the final alignment and identifying and quantifying mutations within a pre-defined sequence distance window from the canonical enzyme-specific cut sites; outputting the final alignment, analysis, and quantification results data as tables or graphics.

Many different arrangements of the various components and processes described herein as well as components or processes not shown, are possible without departing from the spirit and scope of the present disclosure. It should be understood that embodiments or aspects may include and otherwise be implemented by a combination of various hardware, software, or electronic components. For example, various microprocessors and application specific integrated circuits ("ASICs") can be utilized, as can software of a variety of languages Also, servers and various computing devices can be used and can include one or more processing units, one or more computer-readable mediums, one or more input/output interfaces, and various connections (e.g., a system bus) connecting the components.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the methods and processes described herein include all actual or potential combinations of embodiments, aspects, options, examples, and preferences herein described. The methods described herein may omit any component or step, substitute any component or step disclosed herein, or include any component or step disclosed elsewhere herein. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

REFERENCES

1. Pinello, L. et al., "Analyzing CRISPR genome-editing experiments with CRISPResso." *Nat Biotechnol.* 34 (7): 695-697 (2016).
2. Lindsay, H. et al., "CrispRVariants: precisely charting the mutation spectrum in genome engineering experiments," *Nat. Biotechnol.* 34 (7): 701-703 (2015).
3. Labun, K. et al., "Accurate analysis of genuine CRISPR editing events with ampliCan Kornel," *bioRxiv* 249474 (2018); now published in *Genome Research* 29:843-847 (2019)
4. Li, H., "Minimap2: Pairwise alignment for nucleotide sequences," *Bioinformatics* 34 (18): 3094-3100 (2018).
5. Shen, M. W. et al., "Predictable and precise template-free CRISPR editing of pathogenic variants," *Nature* 563 (7733): 646-651 (2018).
6 Hendel, A. et al., "Quantifying genome-editing outcomes at endogenous loci with SMRT sequencing." *Cell Rep.* 7 (1): 293-305 (2014).
7. Iyer, S. et al., "Precise therapeutic gene correction by a simple nuclease-induced double-stranded break," *Nature* 568 (7753): 561-565 (2019).
8. Vu, G. T. H. et al., "Endogenous sequence patterns predispose the repair modes of CRISPR/Cas9-induced DNA double-stranded breaks in *Arabidopsis thaliana*," *Plant J.* 92 (1): 57-67 (2017).
9. Giannoukos, G. et al., "UDiTaS™, a genome editing detection method for indels and genome rearrangements," *BMC Genomics* 19:212 (2018).
10. Robinson, J., "Integrated genomics viewer," *Nat. Biotechnol.* 29 (1), 24-26 (2012).
11. Clement, K. et al., "Analysis and comparison of genome editing using CRISPResso2," *bioRxiv* 1-20 (2018). Now published in *Nat. Biotechnol.* 37 (3): 224-226 (2019)
12. Zetsche, B. et al., "Cpf1 Is a Single RNA-Guided Endonuclease of a Class 2 CRISPR-Cas System," *Cell* 163 (3): 759-771 (2015).
13. Liu, J. J. et al., "CasX enzymes comprise a distinct family of RNA-guided genome editors," *Nature* 566 (7743): 218-223 (2019).

Computer Code

Exemplary code used to generate a 1D scoring matrix for gap open bonus during alignment using psnw.

```
def     self, cut_up, cut_down, rel_cut_pos, ref_amplicon, nuclease,
direction :
    """
    This function takes in an minimum and maximum distance to look for CRISPR variants
(window size)
    and creates a string to introduce weights for gap open bonuses into the psnw
alignment algorithm.
    If there are multiple cuts, any position between the two cuts is weighted equally
    e.g. one cut Cas9
    :param cut_up: 2
    :param cut_down: 6
    :param rel_cut_pos: 4
    :param ref_amplicon: ACTGATCA
    :return: 002342100
```

```
e.g. two cut Cas9
:param cut_up: 2
:param cut_down: 6
:param rel_cut_pos: 4
:param ref_amplicon: ACTGATCA
:return: 001111100
"""
gap_open_string = [ ]
cpfl_enz = list(["CAS12A", "CPF1", "MAD7"])
try:
    # First the program looks to see if there is a second cut site
    if not None in rel_cut_pos:
        for i in range 0, len(ref_amplicon)):
            # If there is a second cut site, everything between the two cuts gets a +1 bonus
            if cut_down <= i <= cut_up:
                gap_open_string.append("1")
            # If the position is not between the two cuts, it gets no bonus
            else:
                gap_open_string.append("0")
        # Execute these functions if there is only one cut site
        else:
        #If the enzyme is Cas9 nuclease, perform the following functions
        if "CAS9" in nuclease.upper:
            for i in range (0, len(ref_amplicon)):
                # The cut site gets a +4 gap open bonus automatically
                if i == int (rel_cut_pos[0]):
                    gap_open_string.append("4")
                # Sites adjacent by 1bp to the cut site and distal from PAM get a +3 gap open bonus
                elif ((direction[0 == "forward") and (i == (int(rel_cut_pos[0])-1))) or \
                        ((direction[0] == "reverse") and (i == (int(rel_cut_pos(0]) + 1))):
                    gap_open_string.append("3")
                # Sites adjacent by 2bp to the cut site distal from PAM get a +2 gap open bonus
                elif ((direction[0] == "forward") and (i == (int(rel_cut_pos[0]) – 2))) or \
                        ((direction(0) == "reverse" and (i == (int(rel_cut_pos[0] + 1))):
                    gap_open_string.append("2")
                # Sites adjacent by 1bp to the cut site proximal from PAM get a +2 gap open bonus
                elif ((direction[0] == "forward") and (i == (int(rel_cut_pos[0]) + 1))) or \
                        ((direction[0] == "reverse" and (i == (int(rel_cut_pos[0] - 1))):
                    gap_open_string.append("2")
                # Sites between the upstream and downstream window get a +1 gap open bonus
                elif cut_down <= i <= cut_up:
                    gap_open_string.apend("1")
                # All other positions get no bonus
                else:
                    gap_open_string.apend("0")
        elif any enzyme in nuclease.upper ( ) for enzyme in cpfl_enz):
            for i in range (0, len ref_amplicon)):
                if direction[0] == "forward":
                    #Sites at the PAM distal cutsite get a +4 bonus
                    if i == (int (rel_cut_pos[0]):
                        gap_open_string.append("4")
                    #Site at the PAM proximal cutsite get a +3 bonus
                    elif i == (int.rel_cut_pos[0])– 4):
                        gap_open.string.append ("3")
                    # Sites adjacent by 1bp to either cut site get a +2 gap open bonus
                    elif (i == (int(rel_cut_pos[0])–5)) \
                            or (i == (int(rel_cut_pos[0]–3))) \
                            or (i == (int(rel_cut_pos[0]) – 1)) \
                            or (i == (int(rel_cut_pos[0]) + 1 ):
                        gap_open_string.append("2")
                    # Sites between the upstream and downstream window get a +1 gap open bonus
                    elif cut_down <= i <= cut_up:
                        gap_open_string.append("1")
                    # All other positions get no bonus
                    else:
                        gap_open_string.append("0")
```

```
            elif direction(0) == "reverse":
                # Sites at the PAM distal cutsite get a +4 bonus
                if i == (int(rel_cut_pos[0])):
                    gap_open_string.append("4")
                # Site at the PAM proximal cutsite get a +3 bonus
                elif i == (int (rel_cut_pos[0]) + 4);
                    gap_open_string.append("3")
                # Sites adjacent by 1bp to either cut site get a +2 gap open bonus
                elif i == (int(rel_cut_pos[0]) + 5)) \
                     or (i == int(rel_cut_pos[0]) + 1)) \
                     or (i == int(rel_cut_pos[0]) - 1)) \
                     or (i == int(rel_cut_pos[0]) + 3)):
                    gap_open_string.append("2")
                # Sites between the upstream and downstream window get a +1 gap open bonus
                elif cut_down <= i <= cut_up:
                    gap_open_string.append("1")
                # All other positions get no bonus
                else:
                    gap_open_string.append("0")
        else:
            print ("Nuclease is not accepted: { }".format(nuclease)
            raise ValueError
    except ValueError:
        print "This value is not valid":
    return "".join(gap_open_string)
```

Exemplary code used to generate 1D scoring matrix for gap extension bonus during alignment using psnw.

```
def get_gap_ext_bonus (self, cut_up, cut_down, rel_cut_pos, ref_amplicon):
    """
    This function takes in an minimum and maximum distance to look for CRISPR variants
(window size)
    and creates a string to introduce weights for gap extension bonuses into the psnw
alignment algorithm.
    If there are multiple cuts, any position between the two cuts is weighted equally
    e.g. one cut Cas9
    :param cut_up: 2
    :param cut_down: 6
    :param rel_cut_pos: 4
    :param ref_amplicon: ACTGATCA
    :return: 001111100
    e.g. two cut Cas9
    :param cut_up: 2
    :param cut_down: 6
    :param rel_cut_pos: 4
    :param ref_amplicon: ACTGATCA
    :return: 001111100
    """
    gap_ext_string = [ ]
    try:
        # First the program looks to see if there is a second cut site
        if not None in rel_cut_pos:
            for i in range (0, len(ref_amplicon)):
                # If there is a second cut site, everything between the two cuts gets a +1 bonus
                if cut_down <= i <= cut_up:
                    gap_ext_string.append("1")
                # If the position is not between the two cuts, it gets no bonus
                else:
                    gap_ext_string.append("0")
        # Execute these functions if there is only one cut site
        else:
            for i in range (0, len(ref_amplicon)):
                # If there is a second cut site, everything between the two cuts gets a +1 bonus
                if i == int(rel_cut_pos[0])):
                    gap_ext_string.append("1")
                elif (i == (int(rel_cut_pos[0])-1)) or (i == (int(rel_cut_pos[0])+1)):
                    gap_ext_string.append("1")
                elif cut_down <+ i <= cut_up:
                    gap_ext_string.append("1")
                else:
                    gap_ext_string.append("0")
```

```
except ValueException :
    print ("This value is not valid")
return "".join(gap_ext_string)
```

What is claimed:

1. A process for identifying and characterizing double-stranded DNA (dsDNA) break repair sites with improved accuracy, the process comprising:
   (a) performing CRISPR-Cas editing in a population of cells or tissue with one or more guide RNAs to produce edited genomic DNA;
   (b) extracting the edited genomic DNA from the population of cells or tissue;
   (c) amplifying the edited genomic DNA using multiplex PCR to produce amplicons enriched for target-site sequences;
   (d) performing next generation sequencing of the amplicons enriched for target-site sequences and obtaining genomic sample sequence data enriched for target-site sequences;
   subsequently executing on a processor the steps of:
   (e) receiving the genomic sample sequence data enriched for target-site sequences comprising a plurality of sequences;
   (f) merging the sample genomic sequence data enriched for target-site sequences and outputting merged sequences;
   (g) developing predicted target-site sequences for the genome containing predicted dsDNA break repair events when a single-stranded or a double-stranded DNA oligonucleotide donor is provided and outputting the predicted target-site sequences;
   (h) binning the merged sequences by their alignment to the genome using a mapper and outputting binned target-read alignments;
   (i) re-aligning the binned target-read alignments from step (h) to the target-site sequences from step (g) using an aligner weighed by a Cas-enzyme-specific position-specific full gap open and gap extension multiple bonus scoring matrix to simultaneously and preferentially align multiple editing events within a defined sequence distance window of the predicted dsDNA break repair events for each Cas enzyme and each guide RNA and producing a final alignment;
      wherein the multiple bonus scoring matrix uses position-specific gap open and gap extension variable penalty vectors to favor alignment of multiple editing events occurring at or near the predicted dsDNA break repair events, and
      the multiple bonus scoring matrix is derived from biological editing data at canonical Cas enzyme cut sites and the position of each guide RNA;
   (j) analyzing the final alignment and identifying and quantifying editing events within the defined sequence distance window of the predicted dsDNA break repair events for each Cas enzyme and each guide RNA; and
   (k) outputting the final alignment, percent editing, percent insertion, percent deletion, or a combination thereof as tables or graphics and selecting one or more guide RNAs with effective CRISPR-Cas editing based on the quantification data from the final alignment, percent editing, percent insertion, percent deletion, or combination thereof; and
   (l) using the one or more selected guide RNAs in further CRISPR-Cas editing experiments.

2. The process of claim 1, wherein the genomic sample sequence data comprises sequences from a population of cells or subjects.

3. The process of claim 1, wherein the Cas enzyme is Cas9 or Cas12a.

4. The process of claim 3, wherein the defined sequence distance window of the predicted dsDNA break repair events for Cas9 is 8 nt.

5. The process of claim 3, wherein the defined sequence distance window of the predicted dsDNA break repair events for Cas12a is 9 nt from an offset center point −3 bp from a PAM distal cut.

6. The process of claim 1, wherein the sequence distance window of the predicted dsDNA break repair events for each Cas enzyme is between 1 nt to 15 nt.

7. The process of claim 1, wherein the Cas-enzyme specific position-specific matrix weights editing events that are closest to the predicted dsDNA break repair events with the lowest gap open or gap extension penalty according to a pre-defined matrix.

8. The process of claim 1, wherein the Cas-enzyme specific position-specific matrix has a gap open penalty of between 0 and +4.

9. The process of claim 1, wherein the Cas-enzyme specific position-specific matrix has a gap extension penalty of 0 or +1.

* * * * *